Jan. 14, 1941. E. S. BOERNER Plant Pat. 437
ROSE PLANT
Filed Sept. 9, 1940
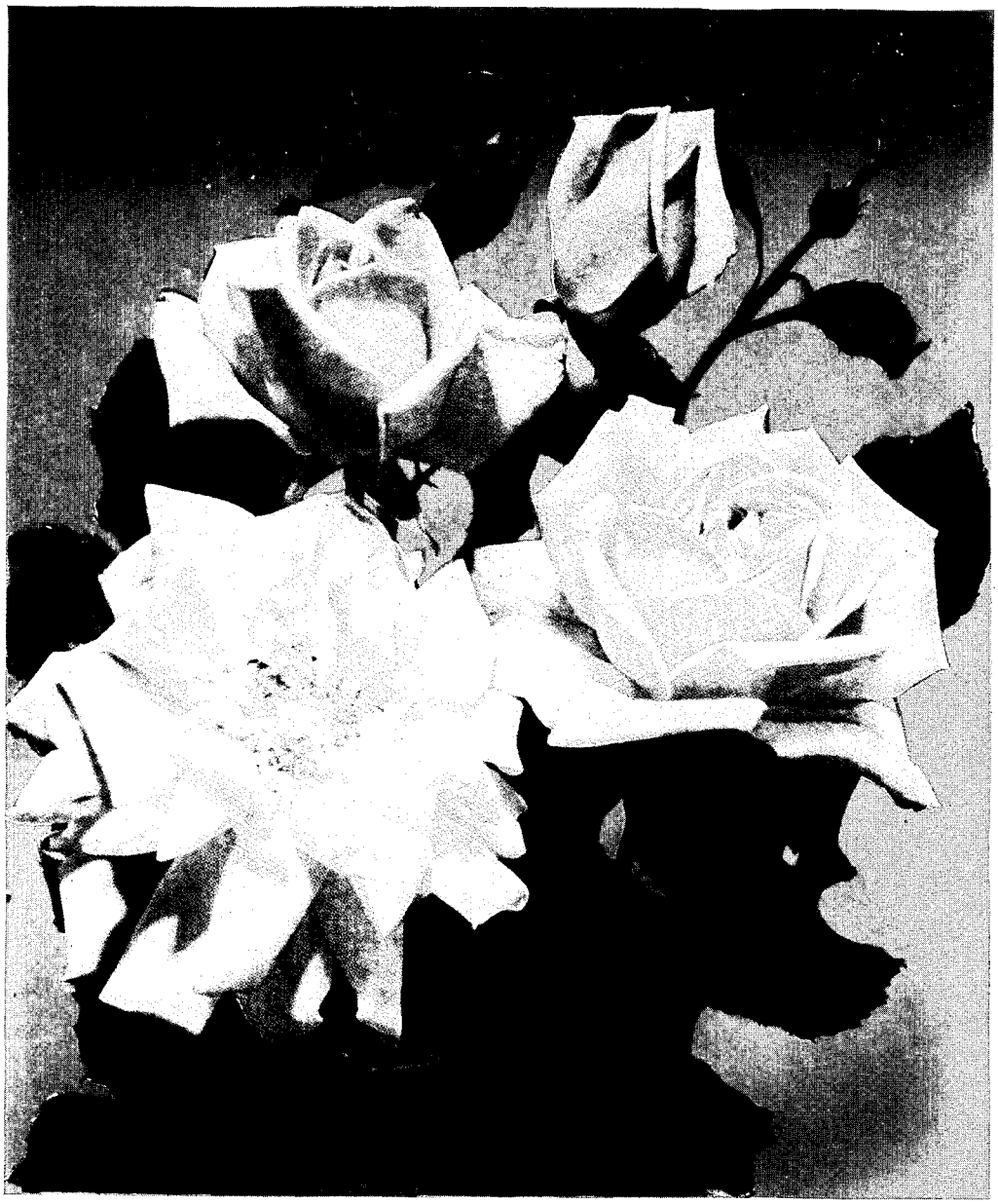
Inventor
E. S. Boerner
By Robb & Robb
attorneys Patented Jan. 14, 1941

Plant Pat. 437

UNITED STATES PATENT OFFICE

437

ROSE PLANT

Eugene S. Boerner, Newark, N. Y., assignor to Jackson & Perkins Company, Newark, N. Y., a corporation of New York Application September 9, 1940, Serial No. 356,076

1 Claim. (Cl. 47—61)

This new and distinct variety of hybrid tea rose plant was discovered by me on a seedling Heinrich Wendland × Max Krause and represents a distinctive improvement over its parent in a number of its features.

Among the novel characteristics, its most important distinction related to its utility lies in the new color combination of its flowers, the petals of which are Flame Scarlet on their reverse, and slightly veined Cadmium Yellow on the inside.

Both its loose open growth and continuous flowering are unusual in roses of this color range.

In structure, the calyx may be said to be nonexistent, and almost flat, the ovaries protruding therefrom, and due to the peculiar formation of the calyx, the ovaries are all in the flower. The petaloids are much lengthened and more prominent than usual.

It is also notable that the young foliage is very dark, in color Hay's Maroon on the upper side and Van Dyke Red on the under side.

The new growth appears to have only a small amount of thorns and the leaf stems lack hooks or prickles.

Asexual reproduction has disclosed that the distinguishing characteristics above referred to come true to form.

The following is a detail description of my new variety, all references to color being in accord with Ridgway's Color Standard:

Parentage: Sport of seedling Heinrich Wendland × Max Krause.

Classification: Botanic and commercial—Hybrid tea.

*Flower*

Blooming habit: Observations made in the fields and gardens of Jackson & Perkins Company, Newark, New York, in the morning of June 28, 1940.

*Recurrent—continuous.*

Bud:

*Size.*—Large.

*Form.*—Long.

Is not affected by wet or hot weather.

*Color.*—When sepals first divide—Flame Scarlet, Plate II. When petals begin to unfurl—between Flame Scarlet, Plate II, and Mars Brown, Plate XV. When half blown: inside of petals—Cadmium Yellow, Plate III, with slight veining of Orange, Plate III; reverse of petals—Flame Scarlet, Plate II.

*Sepals.*—Serrated, branched, "hood" above bud. Curl back when petals unfold. *Color:* outside—Jade Green, Plate XXXI, with tips edged Madder Brown, Plate XIII; inside—Chrysolite Green, Plate XXXI.

*Calyx.—Shape*—very small narrow flat calyx. *Size*—small. *Aspect*—smooth.

*Peduncle.—Length*—long. *Aspect*—slightly prickly. *Color*—Cress Green, Plate XXXI, overlaid with Madder Brown, Plate XIII. *Strength*—bending; heavy.

*Opening.*—Buds open well. Is not affected by adverse conditions.

Bloom:

*Size*—Large. Average size when fully expanded—5½ inches.

*Borne.*—Several together.

*Stems.*—Long; normal.

*Form.—When first open*—cupped. *Permanence*—flattens; outer petals curl back.

*Petalage.*—Double (full but open center). Number of petals under normal conditions—30.

*Color.*—Center of flower—Flame Scarlet, Plate II. Outer petals—Deep Chrome, Plate III. Base of petals (aiglet)—Apricot Yellow, Plate IV. Inside of petals—Deep Chrome, Plate III. Reverse of petals—Bittersweet Orange, Plate II. General tonality from a distance—Orange Chrome, Plate II.

*Discoloration.*—General tonality at end of first day—Orange Chrome, Plate II. Second day—Orange Chrome, Plate II. Third day—Orange, Plate III.

Petals:

*Texture.*—Thick. Is not affected by wet or hot weather.

*Appearance.* — Inside — satiny. Outside — shiny.

*Form.*—Oval.

*Arrangement.*—Informal (with "rags" in center). *Petaloids in center* — many; large.

*Persistence.*—Drop off cleanly.

*Fragrance.*—Slight. *Nature*—Tea (average hybrid tea scent).

*Lasting Quality.*—On the plant and as cut flower—long.

*Genital organs:*

*Stamens, anthers.* — *Size* — large, many. *Color*—Light Cadmium, Plate IV. *Arrangement*—mixed with petaloids.

*Stamens, filaments (threads).—Length*—medium. *Color*—Apricot Yellow, Plate IV.

*Pollen.*—Cadmium Yellow, Plate III.

*Styles.*—Bunched, uneven length; long; thin.
*Stigmas.*—Apricot.
*Ovaries.*—All protruding from calyx.

*Plant*

Form: Bush.
Growth: Vigorous, tall, open, and loose.
Foliage: 5–7 leaflets.
*Size.*—Large.
*Quantity.*—Normal to sparse.
*Color.*—*New Foliage:* upper side—Hay's Maroon, Plate XIII; under side—Van Dyke Red, Plate XIII. *Old Foliage:* upper side—Yew Green, Plate XXXI, with veining of Van Dyke Red, Plate XIII; under side—Jade Green, Plate XXXI, with veining of Pompeian Red, Plate XIII.
*Shape.*—Oval.
*Texture.*—Upper side—glossy; under side—smooth. *Ribs and veins*—light, impressed.
*Edge.*—Serrated (saw toothed).
*Serration.*—Single; small.
*Rachis.*—*Color*—Acajou Red, Plate XIII; under side—smooth.
*Stipules.*—*Length*—medium; smooth.
*Disease resistance.*—Resistant.

Wood:
*New wood.*—*Color*—Snuff Brown, Plate XXIX. *Bark*—smooth.
*Old wood.*—*Color*—Cress Green, Plate XXXI. *Bark*—smooth.

Thorns: (thorns are divided into thorns, prickles, and short needles):
*Thorns.*—*Quantity*—On main stalks from base and on laterals from stalk—ordinary. *Form*—broad base; straight. *Color when young*—Light Jasper Red, Plate XIII. *Position*—irregular.
*Prickles.*—*Quantity.* On main stalks and on laterals—none.
*Short needles.*—*Quantity.* On main stalks and on laterals—none.

I claim:

A new and distinct hybrid tea rose plant, characterized as to novelty by its loose open growth, the color of its young foliage, its continuous blooming habit, and the unusual color combination of the flowers, near absence of calyx causing protrusion of the ovaries into the flower, the long prominent petaloids, the small number of thorns on the new growth and lack of hooks or prickles on the leaf stems, substantially as shown and described.

EUGENE S. BOERNER.